United States Patent [19]

Travers et al.

[11] Patent Number: 5,545,793
[45] Date of Patent: Aug. 13, 1996

[54] SKELETAL ISOMERISATION PROCESS FOR OLEFINS USING AN ALUMINA-BASED COMPOUND

[75] Inventors: Christine Travers, Rueil Malmaison; Jean-Pierre Burzynski, Sainte-Foy-Les-Lyons, both of France

[73] Assignee: Institut Francais Du Petrole, Rueil Malmaison, France

[21] Appl. No.: 360,610

[22] Filed: Dec. 21, 1994

[30] Foreign Application Priority Data

Dec. 22, 1993 [FR] France .................................. 93 15502

[51] Int. Cl.$^6$ ........................................................ C07C 5/27
[52] U.S. Cl. ........................ 585/671; 502/158; 502/355
[58] Field of Search ................... 585/671; 502/355, 502/158

[56] References Cited

U.S. PATENT DOCUMENTS

| 4,038,337 | 7/1977 | Manara et al. | |
|---|---|---|---|
| 4,392,988 | 7/1983 | Dobson et al. | |
| 5,191,145 | 3/1993 | Allen et al. | 585/671 |
| 5,296,437 | 3/1994 | Hietala et al. | 585/671 |
| 5,396,015 | 3/1995 | Fricke et al. | 585/671 |

FOREIGN PATENT DOCUMENTS

| 0190883 | 8/1986 | European Pat. Off. |
| 2249852 | 5/1975 | France |

*Primary Examiner*—Anthony McFarlane
*Attorney, Agent, or Firm*—Millen, White, Zelano, & Branigan, P.C.

[57] ABSTRACT

The invention concerns a process for the skeletal isomerisation of n-olefins containing 4 to 20 carbon atoms, consisting in bringing a feedstock containing the olefins into contact with a catalyst prepared from an alumina-based compound which is treated with a polyoroanosiloxane then heat treated. The quantity of silica introduced is generally between 0.05% and 15% by weight.

26 Claims, No Drawings

SKELETAL ISOMERISATION PROCESS FOR OLEFINS USING AN ALUMINA-BASED COMPOUND

PRIOR ART

The present invention relates to an isomerisation process for olefins containing 4 to 20 carbon atoms, more particularly to the isomerisation of n-butenes to isobutenes and n-pentenes to isopentenes (isoamylenes), using a specific catalyst.

Reducing the amount of alkyl lead in petrol has meant that for a number of years, the refiner has had to incorporate other compounds, in particular alcohols and ethers, into the petrol to increase the octane number. In addition to methanol, which is one of the widest known additives, MTBE (methyltertiobutyl ether) has antiknock properties which increase petrol quality and the octane number to a greater extent than that obtained using methanol. MTBE also has a number of other advantages such as:

a boiling point which is the same as that of the petrol components with the poorest antiknock properties;

a vapour tension which is compatible with the above components:

an excellent pour point:

low solubility in water:

complete miscibility with hydrocarbons etc.

MTBE is normally produced from isobutene and methanol in the following reaction:

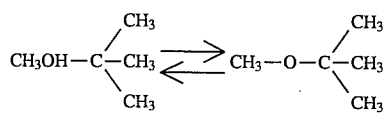

The isobutene is normally contained in $C_3$–$C_4$ olefin cuts from catalytic cracking, steam cracking, thermal cracking and visbreaking effluents. The quantities of isobutene provided by these processes, however, are not sufficient to allow widespread development of the MTBE production process.

For this reason, complete or almost complete isomerisation to isobutenes of the butenes contained in the effluents from the processes mentioned above has been proposed in order to produce larger quantities of isobutene.

Similarly, the manufacture of TAME (tertioamylmethyl ether) requires larger quantities of isopentenes. The invention provides a process for the isomerisation of n-pentenes to isopentenes.

A number of processes and associated catalysts have been described in the literature. The catalysts are normally alumina-based, or more-particularly activated or vapour-treated aluminas. These may be eta or gamma aluminas, halogenated aluminas, bauxite, aluminas treated with boron, silicon or zirconium derivatives, and various aluminosilicates, etc.

The closest prior art is described in U.S. Pat. No. 4,038,337 which relates to a skeletal isomerisation process for olefins containing at least 4 carbon atoms in the presence of an alumina-based catalyst which has; been treated with a silica compound with formula:

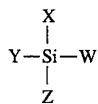

where X, Y, Z and W are selected from the group formed by R, OR, Cl, Br, $SiH_3$, COOR and $SiH_nCl_m$, R representing hydrogen or an alkyl, cycloalkyl, aromatic, alkyl aromatic or alkyl cycloaromatic radical, R containing 1 to 3 carbon atoms, and n and m being equal to 1, 2 or 3.

The silicon compound is used alone or as an organic solution for impregnation.

The majority of these catalysts have a relatively low conversion per pass and low selectivity due to side reactions such as cracking and polymerisation, the latter reactions also involving rapid decrease in performance.

AIM OF THE INVENTION

We have discovered that a catalyst produced from an alumina-based compound prepared by a process wherein, in a first step, the alumina-based substance is treated with an aqueous emulsion of at least one polyorganosiloxane, followed by heat treating the resulting product in a second step, has an improved isoolefin yield (for example isopentene) during skeletal isomerisation of olefins (for example n-pentene). These catalysts also have excellent mechanical and/or thermal properties.

DETAILED DESCRIPTION

In the process of the invention, a pure $C_4$ olefin cut (following removal of the $C_3$ cut), or the whole $C_3$–$C_4$ olefin cut, or preferably a $C_5$ olefin cut, or more generally linear olefinic hydrocarbons containing 4 to 20 carbon atoms per molecule, preferably linear hydrocarbons containing 5 to 20 carbon atoms per molecule, can be isomerised.

The feedstock to be isomerised is brought into contact with the catalyst at a temperature of between 300° C. and 570° C. (preferably between 400° C. and 550° C. when it is constituted by butenes and/or pentenes), at a pressure of between 1 and 10 bars absolute (preferably between 1 and 5 bars absolute when the feedstock is constituted by butenes and/or pentenes).

The space velocity is between 0.1 and 10 $h^{-1}$ expressed as the volume of olefin feedstock per volume of catalyst per hour (preferably between 0.5 and 6 $h^{-1}$ when the feedstock is constituted by butenes and/or pentenes).

The process can be carried out in the presence of water to minimise undesirable secondary reactions, or in the absence of water if the side reactions are not sufficiently important (for a $C_5$ cut or, more generally, $C_5$–$C_{20}$ cuts). The quantity of water introduced into the reactor is such that the $H_2O$/olefinic hydrocarbon molar ratio is between 0 and 10 (advantageously between 0.1 and 10, more particularly between 0.1 and 5 or between 0.1 and 3, and preferably between 0.5 and 3 when the feedstock is constituted by butenes and/or pentenes).

The catalyst is an alumina-based compound prepared by a two step process. In the first step, the alumina-based substance is impregnated with an aqueous emulsion of at least one polyorganosiloxane, the resulting product being heat treated in the second step.

In a first embodiment of the invention, the process is characterised in that in the first step, an alumina-based compound is impregnated with an aqueous emulsion of at least one polyorganosiloxane, the impregnated compound being heat treated in the second step.

Dry impregnation is preferable, ie., the total volume of aqueous emulsion used is approximately equal to the total pore volume of the compound to be impregnated. Thus water may have to be added to the emulsion to obtain the required impregnation volume.

In general, the alumina-based compound contains at least 50%, preferably at least 70% by weight of alumina. The compound is preferably pure alumina.

The starting compound may be in the form of spherules, agglomerates, granulated extrudates, pellets or crushed material. It is preferably in the form of spherules or extrudates.

Alumina spherules manufactured by drop coagulation ("oil-drop" method) may be used as the alumina-based compound, in which the alkali metal content is less than 100 ppm and which preferably has high abrasion resistance. Such an alumina can be prepared in accordance with the processes described in United Kingdom patent GB-B-2 134 536 and European patents EP-B-0 015 801 and EP-B-0 097 539.

The specific surface area of the starting compound, for example alumina, is advantageously between 10 and 450 m²/g, in particular between 60 and 350 m²/g. The pore volume is between 0.3 and 1.2 cm³/g, for example.

In a second embodiment, the process is characterised in that, in the first step, an aqueous emulsion of at least one polyorganosiloxane is introduced during formation of the alumina-based compound, the formed compound containing the polyorganosiloxane being heat treated in the second step.

In this second embodiment, the alumina-based compound can be formed using any technique which is known to the skilled person, in particular mixing-extrusion, drop coagulation ("oil-drop" method) or granulation (coating).

Thus the first step in the second embodiment of the process of the invention comprises the following, for example, depending on the forming method used:

introducing the aqueous emulsion of at least one polyorganosiloxane during mixing of an alumina gel and a peptising agent (such as nitric acid, acetic acid or urea) and optionally water, followed by extrusion to produce extrudates; or introducing the aqueous emulsion of at least one polyorganosiloxane into a suspension or dispersion of alumina before drying in a drop coagulation column, to produce spherules; or introducing the aqueous emulsion of at least one polyorganosiloxane by spraying said emulsion and powdered alumina during granulation (or coating) on a rotary plate to produce granules which are preferably substantially spherical.

In the first step, an alumina-based substance is treated with an aqueous emulsion of at least one polyorganosiloxane which is preferably linear or cyclic. Advantageously, the polyorganosiloxane is substantially insoluble in water.

Preferably, the polyorganosiloxane is a polyorganosiloxane oil.

The polyorganosiloxane can be represented by the following formula (1):

$$R^1R^2{}_2SiO(SiR^2{}_2O)_nSiR^2{}_2R^1 \qquad (1)$$

wherein:

radicals $R^1$ may be identical or different and represent a linear or branched phenyl, alkyl or alkenyl radical containing up to 6 carbon atoms, which may be substituted by at least one cyano group, a hydroxy radical, a $C_1$–$C_4$ alkoxy radical, or a $C_1$–$C_4$ acyloxy radical, radicals $R^2$ may be identical or different and represent a linear or branched phenyl, alkyl or alkenyl radical containing up to 6 carbon atoms, which may be substituted by a cyano radical, n is greater than or equal to 1.

In general, at least 50%, preferably at least 80%, by number of the ensemble of radicals $R^1$ and $R^2$ represent methyl radicals. The most common alkyl or alkenyl radicals are methyl, ethyl, propyl and vinyl radicals. Preferably, a compound with formula (1) is used wherein radicals $R^2$ are identical; the compound is thus a polydiorganosiloxane.

In particular, the polydiorganosiloxane used in the present invention is preferably a polydiorganosiloxane with formula (1) wherein all the $R^2$ radicals are methyl radicals, and radicals $R^1$ are normally identical.

The polyorganosiloxane used in the present invention can thus, for example, be a polydiorganosiloxane with formula (1) wherein all the $R^1$ radicals are hydroxy (HO—) radicals and all the $R^2$ radicals are methyl radicals: the compound with formula (1) is therefore a (bis-hydroxy)polydimethylsiloxane. n is preferably equal to 1 in this case.

The polyorganosiloxane used in the present invention can thus, for example, be a polydiorganosiloxane with formula (1) wherein all the $R^1$ and $R^2$ radicals are methyl radicals: the compound with formula (1) is thus a polydimethylsiloxane, n is preferably equal to 1 in this case.

The polyorganosiloxane normally has a viscosity of less than 50 000 mPa.s at 25° C., in general between 50 and 40,000 mPa.s at 25° C., preferably between 100 and 10,000 mPa.s at 25° C.

A linear polydimethylsiloxane is preferably used, for example with a viscosity of between 100 and 1,000 mPa.s at 25° C.

the polyorganosiloxane used can be a cyclic polyorganosiloxane in which, for example, the radicals are identical, in particular all methyl radicals: hexamethyl-cyclotrisiloxane and octamethyl-cyclotetrasiloxane are particular examples.

In general, the aqueous emulsion of at least one polyorganosiloxane is an anionic or preferably non ionic oil-in-water emulsion; it can be stabilised by an anionic surfactant or, preferably, a non ionic surfactant.

This type of emulsion is well known: it can be prepared by direct polymerisation of the monomer corresponding to the emulsion using a process described in U.S. Pat. Nos. 2,891,920 and 3,294,725. It can also be produced by forming an aqueous emulsion of the polymer, stabilising the emulsion with a surfactant using a process as described in French patent applications FR-A-2 064 563, FR-A-2 094 322 and FR-A-2 114 230, and European patent application EP-A-0 169 098.

Examples of anionic surfactants are alkali metal salts of fatty acids, alkyl phosphates, alkyl sulphates, alkyl sulphonates, aryl sulphonates, alkylaryl sulphonates and sulphosuccinate.

Examples of non ionic surfactants are polyethoxylated fatty alcohols, polyethoxylated alkylphenols and polyethoxylated fatty acids. In general, the emulsion has a dry extract of less than 50% by weight.

The quantity of polyorganosiloxane used in the process of the invention is generally such that the quantity of silica introduced into the alumina-based compound is between 0.05% and 15%, preferably between 0.5% and 5% by weight of silica with respect to the finished product, ie., to the alumina-based compound produced by said process.

In one embodiment of the process of the invention, at least one metallic element from the periodic classification of the elements can be introduced into the starting compound either before, after or simultaneously with the polysiloxane. Non limiting examples of metallic elements are platinum, palladium, nickel, copper, manganese, molybdenum, silver and chromium, and preferably titanium and boron. The alumina-based compound is then a catalyst support, and the catalyst comprises at least the support and the metallic element(s).

In the second step of the process, the impregnated compound is heat treated. The heat treatment is generally carried out at a temperature of between 70° C. and 1200° C.

The heat treatment preferably consists of drying followed by calcining.

Drying is normally carried out at a temperature of between 70° C. and 450° C., for example between 80° C. and 400° C.; the drying period is generally between 0.5 and 6 hours.

Calcining is normally carried out at a temperature of between 450° C. and 1200° C., for example between 500° C. and 900° C.; the calcining period is generally between 1 and 24 hours.

Other drying and calcining conditions are those which are generally employed by the skilled person.

The invention will now be illustrated by the following examples.

The isomerisation performance, for example for butenes, is expressed as follows:

1. Butene conversion
$$C = \frac{\Sigma(\%n\text{-butenes})\text{feedstock} - \Sigma(\%n\text{-butenes})\text{effluent}}{\Sigma(\%n\text{-butenes})\text{feedstock}} \times 100$$

2. Isobutene selectivity
$$S = \frac{(\%\text{isobutene})\text{effluent} - (\%\text{isobutene})\text{feedstock}}{\Sigma(\%n\text{-butenes})\text{feedstock} - \Sigma(\%n\text{-butenes})\text{effluent}} \times 100$$

3. Isobutene yield
$R = C \times S/100$

When the feedstock is composed of pentenes, isomerisation performance is expressed as follows:

1. n-pentene conversion
$$C = \frac{S(\%n\text{-pentenes})\text{feedstock} - S(\%n\text{-pentenes})\text{effluent}}{S(\%n\text{-pentenes})\text{feedstock}} \times 100$$

2. "Tameable"* isopentene selectivity
$$S = \frac{S(\%2M_{C_4}*1 + \%2MC_42)\text{effluent} - (\%2M_{C_4}1 + \%2MC_42)\text{feedstock}}{S(\%n\text{-pentenes})\text{feedstock} - S(\%n\text{-pentenes})\text{effluent}}$$

3. Isopentene yield
$R = C \times S/100$

*Tameable: isomers which react with methanol to produce TAME (tertioamylmethyl ether);
*$2MC_4 1$ = 2-methyl 1-butene;
*$2MC_4 2$ = 2-methyl 2-butene.

The following examples illustrate the invention without limiting its scope.

EXAMPLE 1—CATALYST A IN ACCORDANCE WITH THE INVENTION

The aqueous polyorganosiloxane emulsion used in the examples was RHODORSIL R EMULSION E 1 P, a non ionic aqueous emulsion of a polydimethylsiloxane oil sold by RHONE POULENC CHIMIE. It had a base fluid viscosity (polydimethylsiloxane oil) of about 350 mPa.s at 25° C. and a dry extract of about 35% by weight.

100 grams of alumina extrudate, prepared by mixing-extrusion of an alumina gel followed by drying and calcining, was impregnated with a solution obtained by dissolving 12 grams of RHODORSIL R EMULSION E 1 P with water to a total impregnating volume of 60 cm³.

The impregnated support was then dried for one hour at 140° C. then calcined at 600° C. for two hours.

Alumina extrudates containing 2.85% of $SiO_2$ were thus obtained.

This catalyst was used in the isomerisation of a $C_4$ olefin cut with the composition shown in Table 1. The operational conditions were as follows:

LHSV=2 h⁻¹ (volume of olefin feedstock/volume of catalyst×h)

$H_2O/C_4$=(mole)=2

T=530° C.

p=1.5 bars absolute

Table 1 shows the performances after one hour of operation.

EXAMPLE 2 CATALYST B IN ACCORDANCE WITH THE INVENTION 100 grams of alumina spherules, prepared by drop coagulation of an alumina suspension of by granulation of powdered alumina, was impregnated with a solution obtained by dissolving 12 grams of RHODORSIL R EMULSION E 1 P with water to a total impregnating volume of 60 cm³.

The impregnated support obtained was then dried for one hour at 140° C. then calcined in air at 600° C. for two hours.

Alumina spherules containing 2.9% of $SiO_2$ were thus obtained.

Catalyst B was used in the isomerisation of a $C_4$ olefin cut using the operating conditions described above.

Table 1 shows the performances obtained after one hour of operation.

EXAMPLE 3

Catalysts A and B described in Examples 1 and 2 respectively were used in the isomerisation of n-pentenes under the following conditions:

LHSV=1 h⁻¹

$H_2O/C_5$ (mole)=0

T=410° C.

p=1 bar

The performances after one hour of operation are shown in Table 2.

EXAMPLE 4

Catalysts A and B described in Examples 1 and 2 respectively were used in the isomerisation of n-pentenes under the following conditions:

LHSV=1 h⁻¹

$H_2O/C_5$ (mole)=1

T=410° C.

p=1 bar

The performances after one hour of operation are shown in Table 3.

TABLE 1

| | | | |
|---|---|---|---|
| $H_2O/C_4$ = (mole) | — | 2 | 2 |
| LHSV (h − 1) | — | 2 | 2 |
| Operation | — | 1 | 1 |

TABLE 1-continued

| time (h) % by weight | Feedstock | Catalyst A | Catalyst B |
|---|---|---|---|
| $CH_4$ | 0 | 0.077 | 0.066 |
| $C_2$ | 0 | 0.019 | 0.018 |
| $C_2=$ | 0 | 0.143 | 0.138 |
| $C_3$ | 0 | 0.115 | 0.113 |
| $C_3=$ | 0 | 2.085 | 2.116 |
| $iC_4$ | 0.424 | 0.526 | 0.523 |
| $nC_4$ | 16.662 | 16.716 | 16.702 |
| $C_4=2TR$ | 2.046 | 21.121 | 21.224 |
| $C_4=1$ | 70.59 | 17.342 | 16.802 |
| $iC_4=$ | 6.66 | 23.955 | 24.298 |
| $C_4=2Cis$ | 2.744 | 16.385 | 16.335 |
| $C_4==$ | 0.037 | 0.08 | 0.074 |
| $C_5^+$ | 0.095 | 1.414 | 1.57 |
| Conversion % | — | 27.23 | 27.86 |
| Selectivity % | — | 84.23 | 83.98 |
| Yield % | — | 22.94 | 23.40 |

TABLE 2

|  | Catalyst A | Catalyst B |
|---|---|---|
| Conversion (%) | 70.0 | 70.2 |
| Selectivity (%) | 75.0 | 74.8 |
| Yield | 52.5 | 52.5 |

TABLE 3

|  | Catalyst A | Catalyst B |
|---|---|---|
| Conversion (%) | 63.0 | 62.5 |
| Selectivity (%) | 80.0 | 80.2 |
| Yield | 50.4 | 50.1 |

We claim:

1. A skeletal isomerisation process for olefins containing 4 to 20 carbon atoms, comprising passing a feedstock containing the olefins over a catalyst produced from an alumina-based compound, characterised in that said process is carried out at a temperature of between 300° C. and 570° C., a pressure of between 1 and 10 bars, a space velocity (volume of olefin feedstock per volume of catalyst per hour) of between 0.1 and 10 $h^{-1}$, in the presence of a quantity of water such that the water/olefinic hydrocarbon molar ratio is between 0 and 10, and in that the alumina-based compound is obtained by a process in which, in a first step, an alumina-based substance is treated with an aqueous emulsion of at least one polyorganosiloxane, the resulting product being heat treated in a second step.

2. A process according to claim 1, characterised in that the alumina-based compound contains 0.05% to 15% of silica.

3. A process according to claim 1, characterised in that, in the first step, an alumina-based compound is impregnated with an aqueous emulsion of at least one polyorganosiloxane the impregnated compound being heat treated in the second step.

4. A process according to claim 1, characterised in that the alumina-based starting compound is formed prior to the first step.

5. A process according to claim 1, characterised in that, in the first step, an aqueous emulsion of at least one polyorganosiloxane is introduced during forming of the alumina-based compound the formed compound being heat treated in the second step.

6. A process according to claim 5, characterised in that said forming is carried out by mixing-extrusion, drop coagulation or granulation.

7. A process according to claim 1, characterised in that said polyorganosiloxane is a polyorganosiloxane oil.

8. A process according to claim 1, characterised in that said polyorganosiloxane has the following formula (1):

$$R^1R^2_2SiO(SiR^2_2O)_nSiR^2_2R^1 \qquad (1)$$

wherein:

radicals $R^1$ may be identical or different and represent
 a linear or branched phenyl, alkyl or alkenyl radical containing up to 6 carbon atoms, which may be substituted by at least one cyano group,
 a hydroxy radical,
 a $C_1$–$C_4$ alkoxy radical, or
 a $C_1$–$C_4$ acyloxy radical, radicals $R^2$ may be identical or different and represent a linear or branched phenyl, alkyl or alkenyl radical which may be substituted by a cyano radical, n is greater than or equal to 1.

9. A process according to claim 8, characterised in that said polyorganosiloxane has formula (1) wherein at least 50%, of the radicals $R^1$ and $R^2$ represent methyl radicals.

10. A process according to claim 8, characterised in that radicals $R^1$ are identical and represent hydroxy or methyl radicals, and radicals $R^2$ are methyl radicals.

11. A process according to claim 10, characterised in that n equals 1.

12. A process according to claim 1, characterised in that said polyorganosiloxane is a linear polydimethylsiloxane with a viscosity of less than 50 000 mPa.s at 25° C.

13. A process according to claim 1, characterised in that said polyorganosiloxane is a cyclic polydiorganosiloxane, wherein all the radicals are methyl radicals.

14. A process according to claim 1, characterised in that said aqueous emulsion is non ionic.

15. A process according to claim 1, characterised in that the quantity of polyorganosiloxane used is such that the alumina-based compound produced contains between 0.5% and 5% by weight of silica.

16. A process according to claim 1, characterised in that, in the second step, said heat treatment is carried out at a temperature of between 70° C. and 1200° C.

17. A process according to claim 1, characterised in that, in the second step, said heat treatment comprises drying followed by calcining.

18. A process according to claim 1, characterised in that said alumina based compound obtained constitutes the catalyst.

19. A process according to claim 1, characterised in that said alumina based compound obtained constitutes a catalyst support, said catalyst also containing at least one other element from the periodic classification.

20. A process according to claim 1, characterised in that said alumina based compound obtained constitutes the catalyst support, said catalyst also containing at least one element selected from the group consisting of platinum, palladium, nickel, copper, manganese, molybdenum, silver and chromium.

21. A process according to claim 19, characterised in that said at least one element is selected from the group consisting of titanium and boron.

22. A process according to claim 1, characterised in that said feedstock is a $C_3$ olefin cut and wherein pentenes therein are converted to isopentenes.

23. A process according to claim 1, characterised in that said water/olefinic hydrocarbon molar ratio is between 0.1 and 3.

24. A process according to claim 22, characterised in that said process is carried out in the absence of water.

25. A process according to claim 9, wherein at least 80% of the $R^1$ and $R^2$ radicals represent methyl.

26. A process according to claim 1, wherein the feedstock contains linear butenes which are converted to isobutenes.

* * * * *